US005290658A

United States Patent [19]

[11] Patent Number: 5,290,658

[45] Date of Patent: Mar. 1, 1994

Uenishi et al.

[54] POSITIVE TYPE PHOTORESIST COMPOSITION COMPRISING POLYAROMATIC HYDROXY QUINONE DIAZIDE ESTERS AS THE PHOTOSENSITIVE INGREDIENT

[75] Inventors: Kazuya Uenishi; Yasumasa Kawabe; Tadayoshi Kokubo, all of Shizuoka, Japan

[73] Assignee: Fuji Photo Film Co., Ltd., Kanagawa

[21] Appl. No.: 873,158

[22] Filed: Apr. 24, 1992

[30] Foreign Application Priority Data

Apr. 26, 1991 [JP] Japan .................................. 3-122851

[51] Int. Cl.$^5$ ........................ G03F 7/023; G03F 7/031

[52] U.S. Cl. .................................... 430/192; 430/165; 430/191; 430/193; 430/326; 534/556; 534/557

[58] Field of Search ............... 430/192, 193, 165, 166, 430/191, 326; 534/556, 557

[56] References Cited

U.S. PATENT DOCUMENTS

| | | | |
|---|---|---|---|
| 4,101,323 | 7/1978 | Buhr et al. | 430/270 |
| 4,731,319 | 3/1988 | Kohara et al. | 430/192 |
| 4,906,549 | 3/1990 | Asaumi et al. | 430/192 |
| 5,153,096 | 10/1992 | Uenishi et al. | 430/192 |
| 5,238,775 | 8/1993 | Kajita et al. | 430/192 |

FOREIGN PATENT DOCUMENTS

| | | |
|---|---|---|
| 0358871 | 3/1990 | European Pat. Off. . |
| 0430477 | 6/1991 | European Pat. Off. . |

OTHER PUBLICATIONS

Chemical Abstracts 112: 207951n.

Patent Abstracts of Japan, vol. 13, No. 478, (P-951)(3826), Oct. 30, 1989 & JP-A-1 189 644 (Fuji Photo Film Co., Ltd.), Jul. 28, 1989.

*Primary Examiner*—Richard L. Schilling
*Assistant Examiner*—John S. Chu
*Attorney, Agent, or Firm*—Sughrue, Mion, Zinn, Macpeak & Seas

[57] ABSTRACT

A positive photoresist composition is provided, which comprises an alkali-soluble novolak resin and at least one light-sensitive material represented by formula (III),

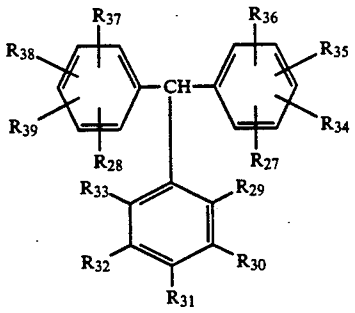

(III)

wherein $R_{27}$ and $R_{28}$ may be the same or different and which represents —OH,

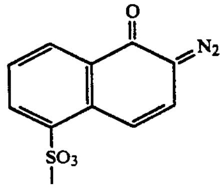

or

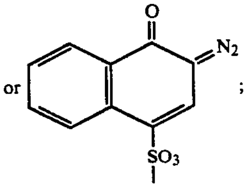

;

$R_{29}$ and $R_{33}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, a cyano group, (Abstract continued on next page.)

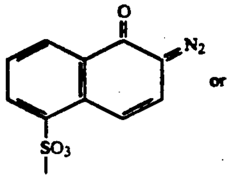
or
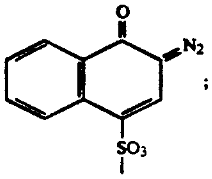
;

$R_{34}$ to $R_{39}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted acyloxy group,

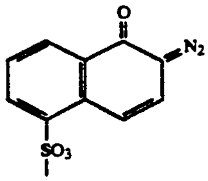
or
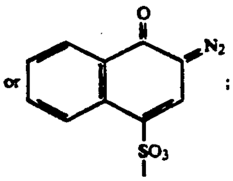
;

with the proviso that the number of

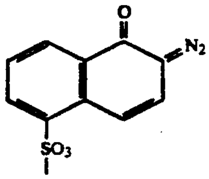
and/or
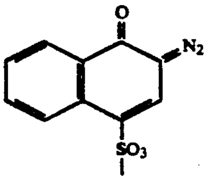

substituent groups is at least 2 and not more than 7, and at least four of $R_{34}$ to $R_{39}$ is a substituent selected from the group consisting of an alkyl group, an alkoxy group, an aryl group, an aralkyl group, and an acyloxy group.

3 Claims, No Drawings

POSITIVE TYPE PHOTORESIST COMPOSITION COMPRISING POLYAROMATIC HYDROXY QUINONE DIAZIDE ESTERS AS THE PHOTOSENSITIVE INGREDIENT

FIELD OF THE INVENTION

The present invention relates to a positive type photoresist composition sensitive to radiation. More particularly, the present invention relates to a photoresist composition for fine work which provides high resolution and sensitivity and has an excellent pattern cross section.

A positive type photoresist of the present invention is coated on a substrate such as a semi-conducting wafer, glass, ceramics and metal by a spin coating method or roller coating method to a thickness of 0.5 to 3 μm. The coat material is then heated and dried. A circuit pattern or the like is printed on the material through an exposure mask by irradiation with ultraviolet rays. The material is then developed to obtain a positive image. Subsequently, the positive image is used as a mask to effect patterned etching on a substrate. Typical applications of a positive type photoresist are production of semiconductors such as IC, production of circuit boards such as liquid crystal and thermal heads, and photofabrication.

BACKGROUND OF THE INVENTION

Generally used positive type photoresist compositions include compositions comprising an alkali-soluble resin and a naphthoquinone diazide compound as a light-sensitive material. Examples of such compositions include novolak type phenol resin/naphthoquinone diazide-substituted compounds as disclosed in U.S. Pat. Nos. 3,666,473, 4,115,128, and 4,173,470. Most typical examples of such compositions include novolak resin made of cresol-formaldehyde/trihydroxybenzophenone-1,2-naphthoquinonediazide sulfonic acid ester as disclosed in L. F. Thompson, "Introduction to Microlithography", ACS, No. 219, pp. 112 -121 (1983).

As a binder, novolak resin can be dissolved in an alkaline aqueous solution without swelling. The novolak resin can also exhibit a high resistance particularly to plasma etching when an image thus produced is used as a mask for etching. Thus, novolak resin is particularly useful in this application.

As a light-sensitive material, naphthoquinone diazide compound serves as a dissolution inhibitor for reducing the alkali solubility of novolak resin but is peculiar in that it decomposes upon irradiation with light to produce an alkali-soluble substance which enhances the alkali solubility of the novolak resin. Because of the great change in properties by irradiation with light, naphthoquinone diazide compound is particularly useful as a light-sensitive material for a positive type photoresist.

Many positive type photoresists comprising a novolak resin and a naphthoquinone diazide light-sensitive material have previously been developed and put into practical use. These positive type photoresists have attained sufficient results in using lines of a width of 1.5 to 2 μm.

However, integrated circuits have increased in their degree of integration. A recent tendency is to use ultrafine patterns formed of lines of a width of 1 μm or less in the production of semiconducting substrates for SLSI circuit and the like. In such an application, a photoresist having a high resolution, a high accuracy of reproduction of exposure mask pattern and a high sensitivity for high productivity has been desired. The above mentioned previously known positive type photoresists cannot meet these requirements.

SUMMARY OF THE INVENTION

It is therefore an object of the present invention to provide a positive type photoresist composition having a high resolution, particularly in the production of semiconductor devices.

It is another object of the present invention to provide a positive type photoresist composition which can provide accurate reproduction of photomask lines over a wide dimensional range, particularly in the production of semiconductor devices.

It is a still further object of the present invention to provide a positive type photoresist composition capable of forming a resist pattern having a cross section with a high aspect ratio in a pattern with a line width of 1 μm or less, particularly in the production of semiconductor devices.

It is a further object of the present invention to provide a positive type photoresist composition capable of forming a pattern having a cross section with nearly vertical sides, particularly in the production of semiconductor devices.

It is a further object of the present invention to provide a positive type photoresist composition having wide development latitude, particularly in the production of semiconductor devices.

It is a still further object of the present invention to provide a positive type photoresist composition which can provide a resist image with excellent heat resistance, particularly in the production of semiconductor devices.

These and other objects of the present invention are accomplished with a positive type photoresist composition, which comprises an alkali-soluble novolak resin and at least one light-sensitive material represented by formulae (I), (II) and (III):

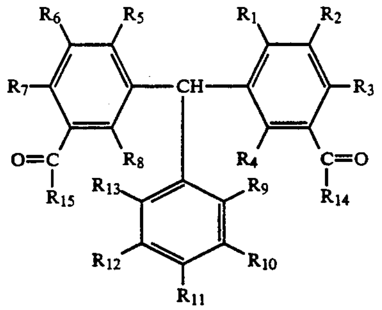

(I)

wherein $R_1$ to $R_{13}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, a cyano group,

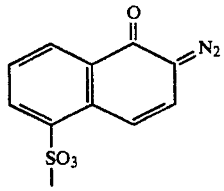
,
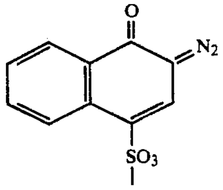

wherein the number of

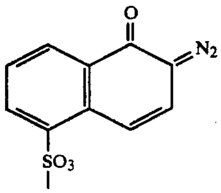
and/or
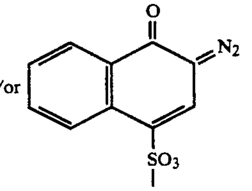

substituent groups is at least 2 and not more than 9, at least one of $R_9$ to $R_{13}$ being a substituent selected from the group consisting of an alkoxy group, an aryloxy group, an aralkyloxy group, an acyl group, an acyloxy group, a halogen, a nitro group, and a cyano group; and $R_{14}$ and $R_{15}$ each represents a substituted or unsubstituted alkyl group, a substituted or unsubstituted aryl group or a substituted or unsubstituted aralkyl group;

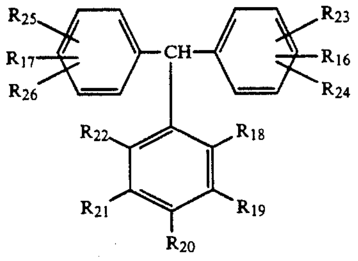
(II)

wherein $R_{16}$ and $R_{17}$ may be the same or different and each represents —OH,

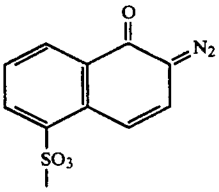
or
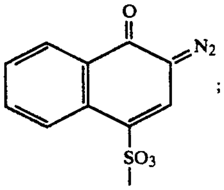
;

$R_{18}$ to $R_{22}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, a cyano group,

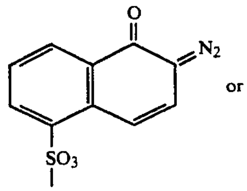
or
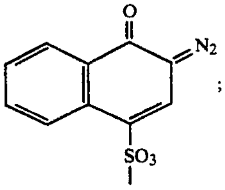
;

$R_{23}$ to $R_{26}$ each represents a substituted or unsubstituted alkyl group, a substituted or unsubstituted aryl group, a substituted or unsubstituted aralkyl group, substituted or unsubstituted alkoxy group, or a substituted or unsubstituted acyloxy group, with the proviso that the number of

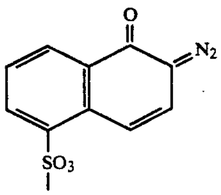
and/or
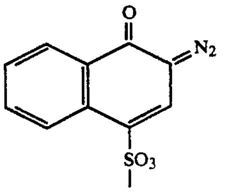

substituent groups is at least 2 and not more than 6, and at least one of $R_{18}$ to $R_{22}$ is a substituent group selected from the group consisting of an alkoxy group, an aryloxy group, an aralkyloxy group, an acyl group, an acyloxy group, a halogen, a nitro group, and a cyano group;

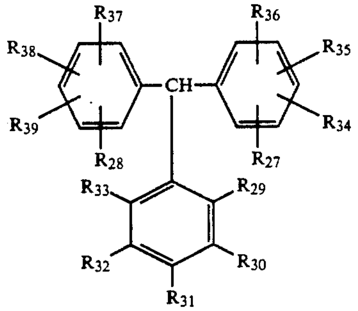
(III)

wherein $R_{27}$ and $R_{28}$ may be the same or different and each represents —OH,

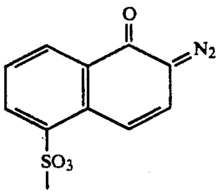
or
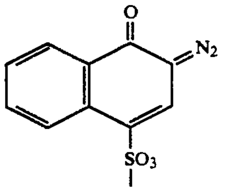

$R_{29}$ and $R_{33}$ may be the same or different to each represents —H, —OH, a substituted or unsubstituted alkyl group, a substituted or unsubststituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, a cyano group,

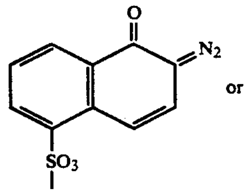
or
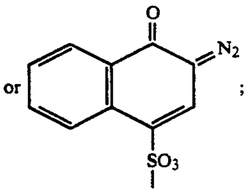
;

$R_{34}$ to $R_{39}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted acyloxy group,

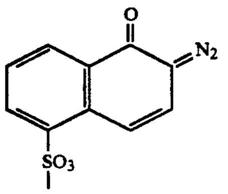
or
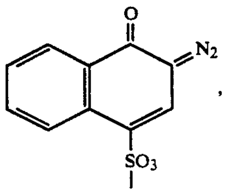
, with the proviso that the number of

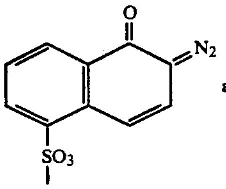
and/or
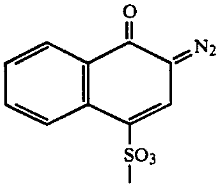

substituent groups is at least 2 and not more than 7, and at least four of $R_{34}$ to $R_{39}$ are a substituent selected from the group consisting of an alkyl group, an alkoxy group, an aryl group, an aralkyl group, and an acyloxy group.

DETAILED DESCRIPTION OF THE INVENTION

The light-sensitive materials represented by formulae (I), (II) and (III) can be obtained by reacting a polyhydroxytriphenylmethane compound represented by formulae (I'), (II') or (III') with 1,2-naphthoquinonediazido-5(and/or -4)-sulfonyl chloride.

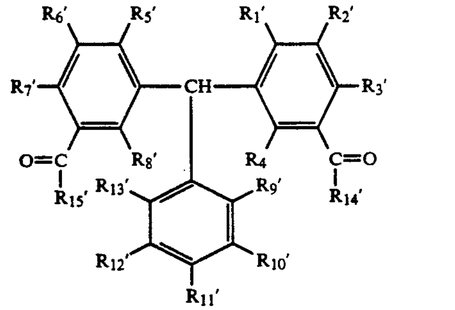
(I')

wherein $R'_1$ to $R'_{13}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, or a cyano group, with the proviso that there are at least 2 and not more than 9 hydroxy substituent groups present, and at least one of $R'_9$ to $R'_{13}$ is a substituent group selected from the group consisting of an alkoxy group, an aryloxy group, an aralkyloxy group, an acyl group, an acyloxy group, a halogen, a nitro group, and a cyano group; and $R'_{14}$ and $R'_{15}$ each represents a substituted or unsubstituted alkyl group, a substituted or unsubstituted aryl group, or a substituted or unsubstituted aralkyl group.

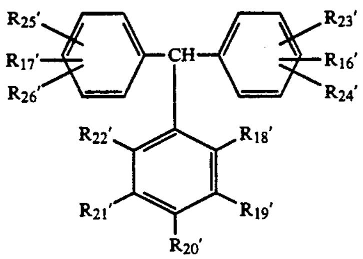
(II')

wherein $R'_{16}$ and $R'_{17}$ each represents —OH; $R'_{18}$ to $R'_{22}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, or a cyano group; $R'_{23}$ to $R'_{26}$ each represents a substituted or unsubstituted alkyl group, a substituted or unsubstituted aryl group, a substituted or unsubstituted aralkyl group, a substituted or unsubstituted alkoxy group, a substituted or unsubstituted acyloxy group, with the proviso that there are at least 2 and not more than 6 hydroxy substituent groups present, and at least one of $R'_{18}$ to $R'_{22}$ is a substituent selected from the group consisting of an alkoxy group, an aryloxy group, an aralkyloxy group, an acyl group, an acyloxy group, a halogen, a nitro group, and a cyano group.

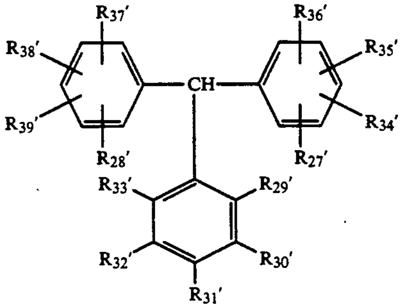
(III')

wherein $R'_{27}$ and $R'_{28}$ each represents —OH; $R'_{29}$ to $R'_{33}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, or a cyano group; $R'_{34}$ to $R'_{39}$ may be the same or different and each represents a substituted or unsubstituted alkyl group, a substituted or unsubstituted aryl group, a substituted or unsubstituted aralkyl group, a substituted or unsubstituted alkoxy group, a substituted or unsubstituted acyloxy group, with the proviso that there are at least 2 and not more than 7 hydroxy substituent groups present, and at least four of $R'_{34}$ to $R'_{39}$ are substituent groups selected from the group consisting of an alkyl group, an alkoxy group, an aryl group, an aralkyl group, and an acyloxy group.

Preferred examples of the groups other than —H and —OH represented by $R'_1$ to $R'_{15}$, $R'_{18}$ to $R'_{26}$, and $R'_{29}$ to $R'_{39}$ include $C_{1-8}$ alkyl and alkoxy groups, and $C_{6-15}$ aryl, aryloxy, aralkyl and aralkyloxy groups; $C_{1-12}$ alkyl and alkoxy groups each containing as a substituent alkoxy group, an aryloxy group, an aryl group, a hydroxyl group, a carboxyl group, a sulfo group, an amino group, a nitro group, a silyl group, a silylether group, a cyano group, an aldehydo group, a mercapto group, or a halogen; $C_{6-15}$ aryl, aryloxy, aralkyl and aralkyloxy groups each containing as a substituent an alkoxy group, an aryloxy group, an aryl group, a hydroxyl group, a carboxyl group, a sulfo group, an amino group, a nitro group, a silyl group, a silylether group, a cyano group, an aldehydo group, a mercapto group, or a halogen; a $C_{2-15}$ aliphatic acyl, aromatic acyl and acyloxy groups, a halogen, a nitro group, and a cyano group.

In formula (II'), $R'_{16}$, $R'_{17}$, and $R'_{23}$ to $R'_{26}$ may be in any position. A preferred structure is as follows:

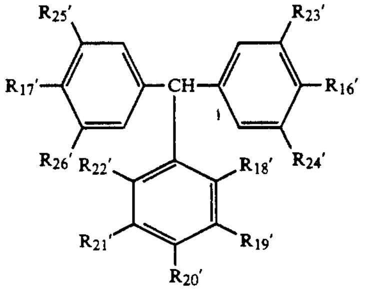

(II")

At least one of $R'_{18}$ to $R'_{22}$ is a substituent selected from the group consisting of substituted or unsubstituted alkoxy, aryloxy, aralkyloxy, acyl and acyloxy groups, a halogen, a nitro group, and a cyano group, preferably a substituted or unsubstituted alkoxy, aryloxy or aralkyloxy group or a nitro group, with a substituted or unsubstituted alkoxy group being particularly preferred.

In formula (III'), at least four, preferably all of $R'_{34}$ to $R'_{39}$ are a substituted or unsubstituted alkyl group, aryl group, aralkyl group or alkoxy group, with a substituted or unsubstituted alkyl group or alkoxy group being particularly preferred.

The polyhydroxytriphenylmethane compound represented by formula (I'), (II') or (III') can be obtained by condensing a substituted or unsubstituted phenol with a substituted or unsubstituted benzaldehyde in accordance with the method proposed by J. E. Driver et al (J. Chem. Soc., PP. 985-989 (1954)).

The esterification reaction of the polyhydroxytriphenylmethane compound represented by formula (I'), (II') or (III') with 1,2-naphthoquinonediazido-5(and/or -4)-sulfonyl chloride can be accomplished by ordinary methods.

In particular, predetermined amounts of a polyhydroxytriphenylmethane compound represented by formula (I'), (II') or (III'), 1,2-naphthoquinonediazido-5(and/or -4)-sulfonyl chloride, and a solvent such as dioxane, acetone, methyl ethyl ketone, r-butyrolactone and N-methylpyrrolidone are charged into a flask. A basic catalyst such as sodium hydroxide, sodium carbonate, sodium bicarbonate and triethylamine is then added dropwise to the material to effect condensation. The resulting product is washed with water, purified, and then dried.

Thus, the light-sensitive material represented by formula (I), (II) or (III) can be prepared as set forth above.

In the above mentioned esterification reaction, mixtures with different esterification degrees and esterification positions are obtained. Therefore, the percentage esterification as used herein is defined as the average of the values of the mixtures.

The thus defined percentage esterification can be controlled by properly selecting the mixing ratio of the starting material (I'), (II') or (III') and 1,2-naphthoquinonediazido-5(and/or -4-)sulfonyl chloride. In other words, since substantially all of 1,2-naphthoquinonediazido-5(and/or -4-)sulfonyl chloride thus added undergoes esterification reaction, the molar ratio of the starting materials may be properly adjusted to obtain a mixture with a desired percentage esterification.

The alkali-soluble novolak resin to be used in the present invention can be obtained by addition condensation of an acidic catalyst in an amount of 0.6 to 1.0 mol per mol of phenol.

Such phenols include phenol, o-cresol, m-cresol, and p-cresol, singly or in combination.

Aldehydes which can be used include formaldehyde, paraformaldehyde, acetaldehyde, halogenated acetaldehyde (e.g., chloroacetaldehyde, bromoacetaldehyde), furfural, etc. Acidic catalysts which can be used include hydrochloric acid, sulfuric acid, formic acid, oxalic acid, acetic acid, or the like.

A novolak resin with a molecular weight of 1,000 to 50,000 thus obtained is alkali soluble.

The proportion of the light-sensitive material to be used in the present invention is preferably 5 to 100 parts by weight, more preferably 10 to 50 parts by weight based on 100 parts by weight of novolak resin. If this value falls below 5 parts by weight, the percentage film remaining is remarkable reduced. If this value exceeds 100 parts by weight, the sensitivity and the solubility in the solvent are reduced.

The above mentioned light-sensitive material should be mainly used in the present invention. However, an ordinary light-sensitive material can be optionally used such as a compound obtained by esterification of, e.g., 2,3,4-trihydroxybenzophenone, 2,4,4'-trihydroxybenzophenone, 2,4,6-trihydroxybenzophenone, 2,3,4,4'-tetrahydroxybenzophenone, and 2,3,4,3',4',5'-hexahydroxybenzophenone with 1,2-naphthoquinonediazido-5-(and/or -4-)sulfonyl chloride.

In this case, such a light-sensitive material may be used in an amount of 100 parts by weight or less, preferably 30 parts by weight or less based on 100 parts by weight of light-sensitive material represented by formula (I), (II) and/or (III).

The composition of the present invention can further comprise a polyhydroxy compound to accelerate solubility in the developer. Preferred examples of such a polyhydroxy compound include phenol, resorcinol, phloroglucinol, 2,3,4-trihydroxybenzophenone, 2,3,4,4'-tetrahydroxybenzophenone, 2,3,4,3',4',5'-hexahydroxybenzophenone, and acetone-pyrogallol condensed resin.

Examples of a solvent for dissolving the light-sensitive material and alkali-soluble novolak resin of the present invention include a ketone such as methyl ethyl ketone and cyclohexanone; a ketoether such as 4-ethoxy-2-butanone and 4-methoxy-4-methyl-2-pentanone; an alcohol ether such as ethylene glycol monomethyl ether and ethylene glycol monoethyl ether; an ether such as dioxane and ethylene glycol dimethyl ether; a cellosolve ester such as methyl cellosolve acetate and ethyl cellosolve acetate; an aliphatic ester such as butyl acetate, methyl lactate and ethyl lactate; a halogenated hydrocarbon such as 1,1,2-trichloroethylene; and a high polarity solvent such as dimethylacetamide, N-methylpyrrolidone, dimethylformamide and dimethyl sulfoxide. These solvents may be used singly or in an admixture.

The positive type photoresist composition of the present invention can optionally comprise a dye, plasticizer, adhesion aid, surface active agent, etc.

Specific examples of such a dye include Methyl Violet, Crystal Violet, and Malachite Green. Specific examples of such a plasticizer include stearic acid, acetal resin, phenoxy resin, and alkyd resin. Specific examples of such an adhesion aid include hexamethyl disilazalane and chloromethyl silane. Specific examples of such a surface active agent include nonylphenoxy poly(ethyleneoxy)ethanol and octylphenoxy poly(ethyleneoxy)ethanol.

The above mentioned positive type photoresist composition can be coated on a substrate for use in the preparation of precision integrated circuit elements (e.g. silicon/silicon dioxide coat) by appropriate means such as a spin and coat method, exposed to light through a predetermined mask, and then developed to obtain an excellent resist.

A developer for the positive type photoresist composition of the present invention can include an aqueous solution of an inorganic alkali such as sodium hydroxide, potassium hydroxide, sodium carbonate, sodium silicate, sodium metasilicate and ammonia, a primary amine such as ethylamine and n-propylamine, a secondary amine such as diethylamine and di-n-butylamine, a tertiary amine such as triethylamine and methyldiethylamine, an alcohol amine such as dimethylethanolamine and triethanolamine, a quaternary ammonium salt such as tetramethylammonium hydroxide and tetraethylammonium hydroxide, a cyclic amine such as pyrrole and piperidine, etc. An alcohol, surface active agent or the like may be added in a proper amount to the aqueous solution of an alkali.

The present invention will be further described in the following example, but the present invention should not be construed as being limited thereto. The percentage (%) indicates value by weight unless otherwise specified.

EXAMPLE

(1) Synthesis of Light-Sensitive Material a 10 g of Compound (a') represented by the following formula:

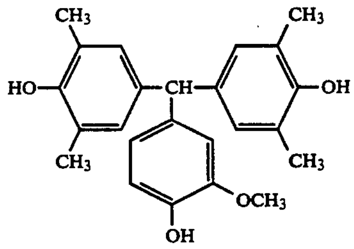

(a')

17.8 g of 1,2-naphthoquinonediazido-5-sulfonyl chloride, and 200 ml of acetone were charged into a three-neck flask for uniform dissolution. A mixture of 7.0 g of triethylamine and 30 ml of acetone was gradually dropwise added to the solution. The reaction system was then allowed to react at 25° C. for 3 hours. The reaction mixture was then poured into 1,000 ml of a 1% aqueous solution of hydrochloric acid. The resulting precipitate was filtered off, washed with water, and then dried at 40° C. to obtain 23.1 g of 1,2-naphthoquinonediazido-5-sulfonic acid ester of Compound (a').

(2) Synthesis of Light-Sensitive Material b 10 g of Compound (b') represented by the following formula:

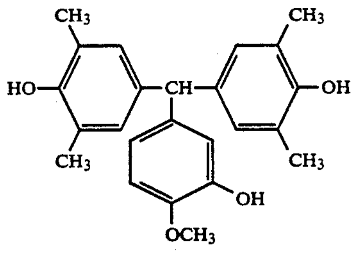

(b')

14.8 g of 1,2-naphthoquinonediazido-5-sulfonyl chloride, and 170 ml of acetone were charged into a three-neck flask for uniform dissolution. A mixture of 5.8 g of triethylamine and 25 ml of acetone was gradually dropwise added to the solution. The reaction system was then allowed to react at 25° C. for 3 hours. The reaction mixture was then poured into 800 ml of a 1% aqueous solution of hydrochloric acid. The resulting precipitate was filtered off, washed with water, and then dried at 40° C. to obtain 21.1 g of 1,2-naphthoquinonediazido-5-sulfonic acid ester of Compound (b').

(3) Synthesis of Light-Sensitive Material c 10 g of Compound (c') represented by the following formula:

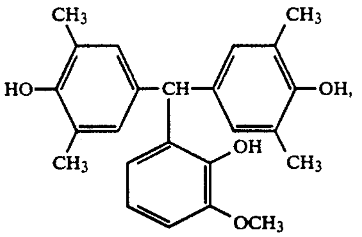

(c')

14.8 9 of 1,2-naphthoquinonediazido-5-sulfonyl chloride, and 170 ml of acetone were charged into a three-neck flask for uniform dissolution. A mixture of 5.8 g of triethylamine and 25 ml of acetone was gradually dropwise added to the solution. The reaction system was then allowed to react at 25° C. for 3 hours. The reaction mixture was then poured into 850 ml of a 1% aqueous solution of hydrochloric acid. The resulting precipitate was filtered off, washed with water, and then dried at a temperature of 40° C. to obtain 19.8 g of 1,2-naphthoquinonediazido-5-sulfonic acid ester of Compound (c').

(4) Synthesis of Light-Sensitive Material d 10 g of Compound (d') represented by the following formula:

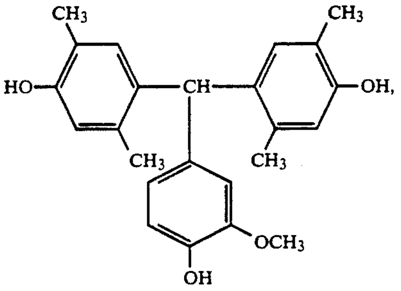

(d')

11.1 g of 1,2-naphthoquinonediazido-5-sulfonyl chloride, and 130 ml of acetone were charged into a three-neck flask for uniform dissolution. A mixture of 4.3 g of triethylamine and 20 ml of acetone was gradually dropwise added to the solution. The reaction system was then allowed to react at 25° C. for 3 hours. The reaction mixture was then poured into 700 ml of a 1% aqueous solution of hydrochloric acid. The resulting precipitate was filtered off, washed with water, and then dried at 40° C. to obtain 17.3 g of 1,2-naphthoquinonediazido-5-sulfonic acid ester of Compound (d').

(5) Synthesis of Light-Sensitive Material e 10 g of Compound (e') represented by the following formula:

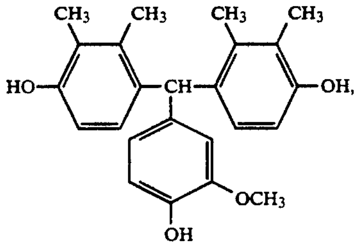

(e')

20.0 g of 1,2-naphthoquinonediazido-5-sulfonyl chloride, and 230 ml of acetone were charged into a three-neck flask for uniform dissolution. A mixture of 7.7 g of triethylamine and 40 ml of acetone was gradually dropwise added to the solution. The reaction system was then allowed to react at 25° C. for 3 hours. The reaction mixture was then poured into 1,300 ml of a 1% aqueous solution of hydrochloric acid. The resulting precipitate was filtered off, washed with water, and then dried at 40° C. to obtain 24.0 g of 1,2-naphthoquinonediazido-5-sulfonic acid ester of Compound (e').

(6) Synthesis of Light-Sensitive Material f 10 g of Compound (f') represented by the following formula:

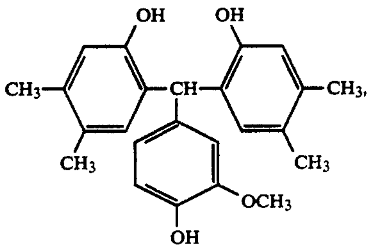

(f')

14.8 g of 1,2-naphthoquinonediazido-5-sulfonyl chloride, and 170 ml of acetone were charged into a three-neck flask for uniform dissolution. A mixture of 5.7 g of triethylamine and 30 ml of actone was gradually dropwise added to the solution. The reaction system was then allowed to react at 25° C. for 3 hours. The reaction mixture was then poured into 1,000 ml of a 1% aqueous solution of hydrochloric acid. The resulting precipitate was filtered off, washed with water, and then dried at 40° C. to obtain 20.0 g of 1,2-naphthoquinonediazido-5-sulfonic acid ester of Compound (f').

(7) Synthesis of Light-Sensitive Material g 10 g of Compound (g') represented by the following formula:

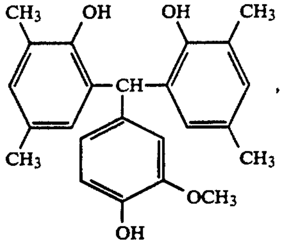

(g')

15.6 g of 1,2-naphthoquinonediazido-5-sulfonyl chloride, and 180 ml of acetone were charged into a three-neck flask for uniform dissolution. A mixture of 6.1 g of triethylamine and 30 ml of acetone was gradually dropwise added to the solution. The reaction system was then allowed to react at 25° C. for 3 hours. The reaction mixture was then poured into 1,100 ml of a 1% aqueous solution of hydrochloric acid. The resulting precipitate was filtered off, washed with water, and then dried at 40° C. to obtain 21.0 g of 1,2-naphthoquinonediazido-5-sulfonic acid ester of Compound (g').

(8) Synthesis of Light-Sensitive Material h 10 g of Compound (h') represented by the following formula:

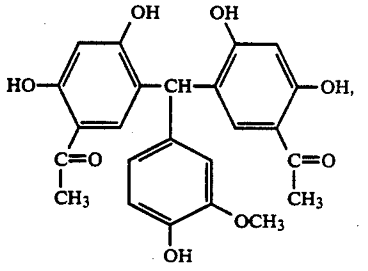

(h')

24.5 g of 1,2-naphthoquinonediazido-5-sulfonyl chloride, and 290 ml of acetone were charged into a three-neck flask for uniform dissolution. A mixture of 9.5 g of triethylamine and 50 ml of acetone was gradually dropwise added to the solution. The reaction system was then allowed to react at 25° C. for 3 hours. The reaction mixture was then poured into 1,600 ml of a 1% aqueous solution of hydrochloric acid. The resulting precipitate was filtered off, washed with water, and then dried at 40° C. to obtain 28.3 g of 1,2-naphthoquinonediazido-5-sulfonic acid ester of Compound (h').

(9) Synthesis of Light-Sensitive Material i 10 g of Compound (i') represented by the following formula:

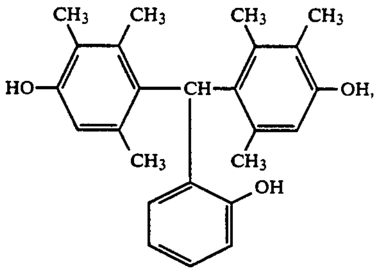

(i')

14.3 g of 1,2-naphthoquinonediazido-5-sulfonyl chloride, and 170 ml of acetone were charged into a three-neck flask for uniform dissolution. A mixture of 5.5 g of triethylamine and 30 ml of acetone was gradually dropwise added to the solution. The reaction system was then allowed to react at 25° C. for 3 hours. The reaction mixture was then poured into 1,000 ml of a 1% aqueous solution of hydrochloric acid. The resulting precipitate was filtered off, washed with water, and then dried at 40° C. to obtain 20.0 g of 1,2-naphthoquinonediazido-5-sulfonic acid ester of Compound (i').

(10) Synthesis of Light-Sensitive Material j 10 g of Compound (j') represented by the following formula:

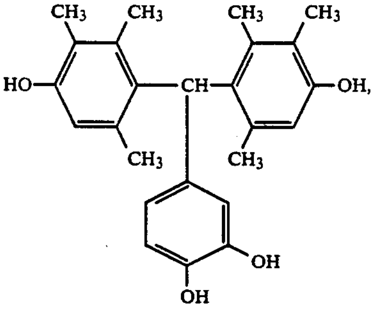

(j')

20.6 g of 1,2-naphthoquinonediazido-5-sulfonyl chloride, and 250 ml of acetone were charged into a three-neck flask for uniform dissolution. A mixture of 8.0 g of triethylamine and 50 ml of acetone was gradually dropwise added to the solution. The reaction system was then allowed to react at 25° C. for 3 hours. The reaction mixture was then poured into 1,500 ml of a 1% aqueous solution of hydrochloric acid. The resulting precipitate was filtered off, washed with water, and then dried at 40° C. to obtain 25.4 g of 1,2-naphthoquinonediazido-5-sulfonic acid ester of Compound (j').

(11) Synthesis of Light-Sensitive Material k 10 g of Compound (k') represented by the following formula:

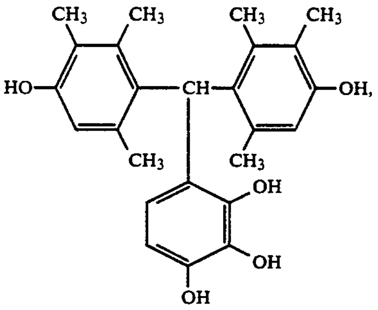

(k')

25.0 g of 1,2-naphthoquinonediazido-5-sulfonyl chloride, and 300 ml of acetone were charged into a three-neck flask for uniform dissolution. A mixture of 9.7 g of triethylamine and 60 ml of acetone was gradually dropwise added to the solution. The reaction system was then allowed to react at 25° C. for 3 hours. The reaction mixture was then poured into 2,000 ml of a 1% aqueous solution of hydrochloric acid. The resulting precipitate was filtered off, washed with water, and then dried at 40° C. to obtain 28.7 g of 1,2-naphthoquinonediazido-5-sulfonic acid ester of Compound (k').

(12) Synthesis of Light-Sensitive Material l 10 g of Compound (l') represented by the following formula:

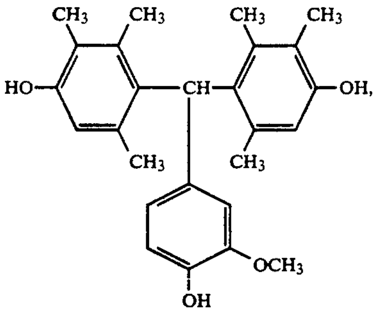

(l')

14.6 g of 1,2-naphthoquinonediazido-5-sulfonyl chloride, and 170 ml of acetone were charged into a three-neck flask for uniform dissolution. A mixture of 5.7 g of triethylamine and 20 ml of acetone was gradually dropwise added to the solution. The reaction system was then allowed to react at 25° C. for 3 hours. The reaction mixture was then poured into 1,200 ml of a 1% aqueous solution of hydrochloric acid. The resulting precipitate was filtered off, washed with water, and then dried at 40° C. to obtain 20.4 g of 1,2-naphthoquinonediazido-5-sulfonic acid ester of Compound (l').

(13) Synthesis of Light-Sensitive Material m 10 g of Compound (m') represented by the following formula:

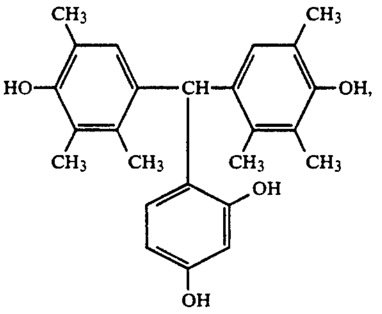

(m')

13.7 g of 1,2-naphthoquinonediazido-5-sulfonyl chloride, and 160 ml of acetone were charged into a three-neck flask for uniform dissolution. A mixture of 5.3 g of triethylamine and 20 ml of acetone was gradually dropwise added to the solution. The reaction system was then allowed to react at 25° C. for 3 hours. The reaction mixture was then poured into 1,200 ml of a 1% aqueous solution of hydrochloric acid. The resulting precipitate was filtered off, washed with water, and then dried at 40° C. to obtain 19.4 g of 1,2-naphthoquinonediazido-5-sulfonic acid ester of Compound (m').

(14) Synthesis of Light-Sensitive Material n
(Comparative Example 1)

10 g of Compound (n') represented by the following formula:

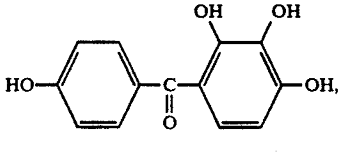

(n')

30.0 g of 1,2-naphthoquinonediazido-5-sulfonyl chloride, and 350 ml of acetone were charged into a three-neck flask for uniform dissolution. A mixture of 11.6 g of triethylamine and 45 ml of acetone was gradually dropwise added to the solution. The reaction system was then allowed to react at 25° C. for 3 hours. The reaction mixture was then poured into 2,600 ml of a 1% aqueous solution of hydrochloric acid. The resulting precipitate was filtered off, washed with water, and then dried at 40° C. to obtain 33.0 g of 1,2-naphthoquinonediazido-5-sulfonic acid ester of Compound (n').

(15) Synthesis of light-sensitive material o
(Comparative Example 2)

10 g of Compound (o') represented by the following formula:

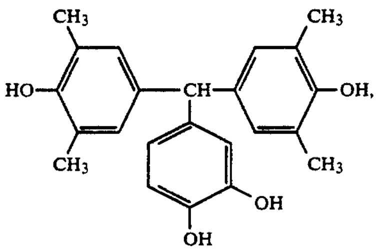

(o')

17.0 g of 1,2-naphthoquinonediazido-5-sulfonyl chloride and 200 ml of acetone were charged into a three-neck flask for uniform dissolution. A mixture of 6.6 g of triethylamine and 26 ml of acetone was gradually dropwise added to the solution. The reaction system was then allowed to react at 25° C. for 3 hours. The reaction mixture was then poured into 1,400 ml of a 1% aqueous solution of hydrochloric acid. The resulting precipitate was filtered off, washed with water, and then dried at 40° C. to obtain 22.3 g of 1,2-naphthoquinonediazide-5-sulfonic ester of Compound (o').

(16) Synthesis of Light-Sensitive Material p
(Comparative Example 3)

10 g of Compound (p') represented by the following formula:

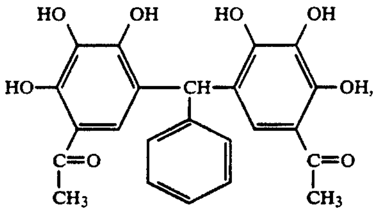

(p')

28.5 g of 1,2-naphthoquinonediazido-5-sulfonyl chloride, and 340 ml of acetone were charged into a three-neck flask for uniform dissolution. A mixture of 11.1 g of triethylamine and 45 ml of acetone was gradually dropwise added to the solution. The reaction system was then allowed to react at 25° C. for 3 hours. The reaction mixture was then poured into 2,400 ml of a 1% aqueous solution of hydrochloric acid. The resulting precipitate was filtered off, washed with water, and then dried at 40° C. to obtain 31.8 g of 1,2-naphthoquinonediazido-5-sulfonic acid ester of Compound (p').

(17) Synthesis of Novolak Resin 37 g of m-cresol, 63 g of p-cresol, 50.5 g of a 37% aqueous solution of formalin and 0.05 g of oxalic acid were charged into a three-neck flask, and then heated with stirring to 100° C. where it was allowed to react for 7 hours.

After completion of the reaction, the reaction system was allowed to cool to room temperature and its pressure was reduced to 30 mmHg. The reaction system was then heated to 150° C. to remove water and unreacted monomers. The resulting novolak resin had a weight-average molecular weight of 7,000 as calculated in terms of polystyrene.

(18) Preparation and Evaluation of Positive Type Photoresist Composition 1.25 of each of the light-sensitive materials a to p as obtained in the synthesis process (1) to (16) above and 5 g of the cresol novolak resin (molecular weight: 7,000) as obtained in the synthesis process (17) above were dissolved in 15 g of ethyl cellosolve acetate. The materials were then filtered out through a microfilter with 0.2-μm diameter pores to prepare photoresist compositions Examples 1 to 13, Comparative Examples 1 to 3.

These photoresist compositions were each coated on a silicon wafer by means of a spinner. The coated materials were each dried at 90° C. for 30 minutes in an atmosphere of nitrogen in a convection oven to obtain resist films with a thickness of 1.2 μm.

These films each was exposed to light by means of a reduction exposure apparatus (NSR1505 available from Nikon K.K.), developed with a 2.38% aqueous solution of tetramethylammonium hydroxide for 1 minute, washed with water for 30 minutes, and then dried.

These resist patterns formed on the silicon wafer were observed and evaluated under a scanning electron microscope. The results are set forth in Table 1.

The sensitivity is defined as the reciprocal of the exposure reproducing a 1.0-μm width mask pattern and represented as relative to that of Comparative Example 1.

The percentage film remaining represents the percentage of the ratio of the amount of film present after development to that before development on the unexposed portion.

The resolving power represents the critical resolving power at the exposure reproducing a 1.0-μm width mask pattern.

The heat resistance is defined as the temperature at which a silicon wafer on which a resist has been patterned can be baked in a convection oven for 30 minutes without pattern deformation.

The resist shape is defined as the angle (θ) made by the side wall of the cross section of a 1.0-μm width resist pattern and the plane of the silicon wafer.

The results show that the resists prepared from the present light-sensitive materials a to m are excellent particularly in resolving power, heat resistance and resist shape.

The light-sensitive materials of the present invention are also excellent in solubility in ethylene glycol monoethyl ether acetate. No precipitation occurred with these resist composition solutions comprising these light-sensitive materials even after standing at 40° C. for 30 days. However, precipitation occurred with the resist composition solution comprising the comparative light-sensitive material n in the resist composition under the same conditions.

TABLE 1

| | | Evaluation | | | | |
|---|---|---|---|---|---|---|
| | Light-Sensitive Material | Relative Sensitivity | Percentage Film Remaining (%) | Resolving Power (μm) | Heat Resistance | Resist Shape (θ) |
| Example 1 | a | 1.2 | 100 | 0.6 | 150 | 88 |
| Example 2 | b | 1.3 | 100 | 0.6 | 145 | 88 |
| Example 3 | c | 1.5 | 99 | 0.6 | 145 | 88 |
| Example 4 | d | 1.5 | 99 | 0.6 | 145 | 88 |
| Example 5 | e | 1.2 | 100 | 0.6 | 150 | 89 |
| Example 6 | f | 1.3 | 99 | 0.6 | 145 | 88 |
| Example 7 | g | 1.3 | 99 | 0.6 | 150 | 88 |
| Example 8 | h | 1.2 | 100 | 0.6 | 150 | 88 |
| Example 9 | i | 1.2 | 100 | 0.6 | 155 | 89 |
| Example 10 | j | 1.3 | 100 | 0.6 | 155 | 89 |
| Example 11 | k | 1.5 | 100 | 0.6 | 155 | 89 |
| Example 12 | l | 1.2 | 100 | 0.6 | 155 | 89 |
| Example 13 | m | 1.3 | 100 | 0.6 | 155 | 89 |
| Comparative Example 1 | n | 1.0 | 97 | 0.8 | 130 | 82 |
| Comparative Example 2 | o | 1.1 | 99 | 0.7 | 140 | 87 |
| Comparative Example 3 | p | 1.1 | 98 | 0.7 | 140 | 87 |

The positive type photoresist composition of the present invention is excellent in resolving power, faithful reproducibility, cross section of resist image, development latitude, heat resistance, and storage stability of the composition solution and is preferred as a photoresist for fine working.

While the invention has been described in detail and with reference to specific embodiments thereof, it will be apparent to one skilled in the art that various changes and modifications can be made therein without departing from the spirit and scope thereof.

What is claimed is:

1. A positive photoresist composition, which comprises, in admixture: an alkali-soluble novolak resin and at least one light-sensitive material represented by formula:

(III)

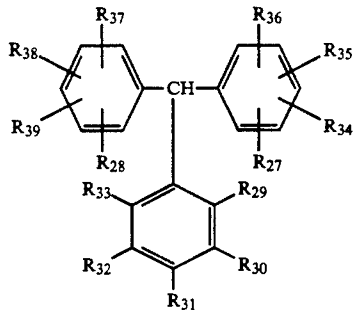

wherein $R_{27}$ and $R_{28}$ may be the same or different and each represents —OH,

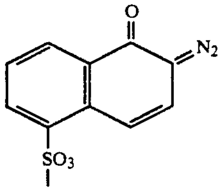
and/or
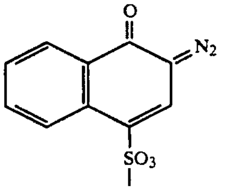

$R_{29}$ to $R_{33}$ may be the same or different and each represents —H, —OH, a substituted or unsubstituted alkyl group, a substituted or unsubstituted aryl group, a substituted or unsubstituted aralkyl group, a substituted or unsubstituted alkoxy group, a substituted or unsubstituted aryloxy group, a substituted or unsubstituted aralkyloxy group, a substituted or unsubstituted acyl group, a substituted or unsubstituted acyloxy group, a halogen, a nitro group, a cyano group,

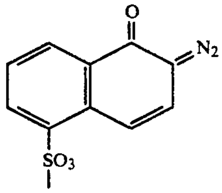
or
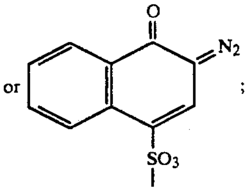
;

$R_{34}$ to $R_{39}$ may be the same or different and each represents —H, —OH; a substituted or unsubstituted alkyl group, a substituted or unsubstituted aryl group, a substituted or unsubstituted aralkyl group, a substituted or unsubstituted alkoxy group, a substituted or unsubstituted acyloxy group,

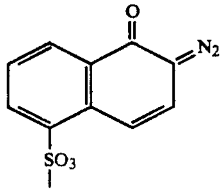
or
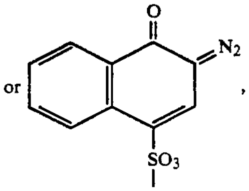
, with the proviso that the number of

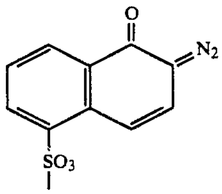
and/or
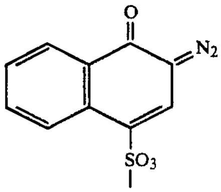

substituent groups is at least 2 and not more than 7, and at least five of $R_{34}$ to $R_{39}$ are a substituent selected from the group consisting of an alkyl group, an alkoxy group, an aryl group, an aralkyl group, and an acyloxy group.

2. A positive type photoresist composition as in claim 1, wherein the light-sensitive material is present in an amount of from 5 to 100 parts by weight based on 100 parts by weight of the novolak resin.

3. A positive type photoresist composition as in claim 2, wherein the light-sensitive material is present in an amount of from 10 to 50 parts by weight based on 100 parts by weight of the novolak resin.

* * * * *

UNITED STATES PATENT AND TRADEMARK OFFICE
CERTIFICATE OF CORRECTION

PATENT NO. : 5,290,658

DATED : March 1, 1994

INVENTOR(S) : Kazuya Uenishi, Yasumasa Kawabe and Tadayoshi Kokubo

It is certified that error appears in the above-identified patent and that said Letters Patent is hereby corrected as shown below:

Please amend Claim 1 as follows:

Column 20, line 11, after "represents", delete "-H, -OH:";

line 39, after "more than 7", insert --.-- (a period);

lines 40-43, delete in their entirety.

Signed and Sealed this

Fifth Day of July, 1994

Attest:

Bruce Lehman

BRUCE LEHMAN

Attesting Officer

Commissioner of Patents and Trademarks